(12) United States Patent
Reed

(10) Patent No.: US 10,993,728 B2
(45) Date of Patent: May 4, 2021

(54) PRECISION BONE DRILL BIT

(71) Applicant: SMV PRECISION INSTRUMENTS, LLC, Austin, TX (US)

(72) Inventor: Gary Reed, Turlock, CA (US)

(73) Assignee: Maestro Logistics, LLC, Austin, TX (US)

(*) Notice: Subject to any disclaimer, the term of this patent is extended or adjusted under 35 U.S.C. 154(b) by 97 days.

(21) Appl. No.: 15/856,347

(22) Filed: Dec. 28, 2017

(65) Prior Publication Data
US 2019/0201009 A1 Jul. 4, 2019

(51) Int. Cl.
*A61B 17/16* (2006.01)
*A61B 90/00* (2016.01)
*A61B 17/00* (2006.01)

(52) U.S. Cl.
CPC ...... *A61B 17/1617* (2013.01); *A61B 17/1615* (2013.01); *A61B 17/162* (2013.01); *A61B 2017/00477* (2013.01); *A61B 2017/00836* (2013.01); *A61B 2017/00982* (2013.01); *A61B 2090/035* (2016.02)

(58) Field of Classification Search
CPC ............................. A61B 17/16; A61B 17/1617
See application file for complete search history.

(56) References Cited

U.S. PATENT DOCUMENTS

| | | | | |
|---|---|---|---|---|
| 3,779,664 A | * | 12/1973 | Caley | B23B 51/02 408/225 |
| 5,273,380 A | * | 12/1993 | Musacchia | B23B 51/02 408/227 |
| 9,447,803 B1 | | 9/2016 | Fu et al. | |
| 2005/0214711 A1 | * | 9/2005 | Buchanan | A61C 5/42 433/102 |
| 2008/0097436 A1 | * | 4/2008 | Culbert | A61B 17/7064 606/86 A |
| 2011/0268518 A1 | * | 11/2011 | Sampath | B23P 15/32 408/59 |
| 2016/0000469 A1 | | 1/2016 | Mueller | |

FOREIGN PATENT DOCUMENTS

EP  1 396 303  3/2004
WO  WO 2012/068641  5/2012

* cited by examiner

*Primary Examiner* — Christopher J Beccia
(74) *Attorney, Agent, or Firm* — Womble Bond Dickinson (US) LLP

(57) ABSTRACT

An orthopedic drill bit includes a cutting head formed to include diametrically opposed cutting lips leading to a central point and away to a radiused periphery to center said bit. The drill includes flutes extending from a cutting end, said flutes having a dulled periphery to prevent out of round holes. The flute design increases in width progressively from the tip up the shank, to maintain an adequate and unrestricted space for chips to easily move upward, preventing the chips from being compressed into a smaller opening while maintaining the tapered depth of the flutes for strength.

4 Claims, 4 Drawing Sheets

PRECISION BONE DRILL BIT

FIELD OF THE INVENTION

The present invention relates generally to an improved drill bit used for drilling holes in living bone. More particularly, this invention relates to drilling holes with hand held power drills that utilize common AO quick release couplers. The manufacturing process involves producing this new drill bit in two separate pieces which results in reduction in cost and needless scrapping of excessive expensive stainless steel required to hold a cutting edge during use.

BACKGROUND

Drilling straight, round holes using a hand held power drill often results in a less than desired outcome. Current drillbit technologies often perform poorly, resulting in holes with negative issues such as, oblong, oversized and misaligned holes often with packed flutes in the drill bit and over-heated surrounding bone.

An even bigger problem of a poor cutting drill bit in the operating room is excessive plunging through the back side of the bone. Plunging or breakthrough does serious damage to vital soft tissues suck as veins, arteries, muscles, tendons ligaments and other bones. Any of these issues can result in extended healing time and even non-union of a fracture than can result in amputation. Current drillbits being used every day fail to address these vital issues.

This invention addresses all of these issues while helping to reduce the cost to the end user of the drill bit by making it in two pieces which is faster and less wasteful.

SUMMARY

In the present invention, the cutting and chip removal features present new and novel shapes and forms not common in other orthopedic drillbits in use today. A sharp drill bit starts easily at angles other than 90 degrees from the surface of the bone, which is rarely flat to start with. A single sharp point at the apex of the two cutting lips can easily push into the surface of the bone at required angles and get the bit started at the exact spot desired by the surgeon. This controls the direction, and roundness of the hole until the full diameter of the bit cuts into the surface of the bone.

The outside diameter of the drillbit is completely cylindrical and absent of common margins and undercut reliefs that follow the edges of the flutes which would enhance the bit's ability to side cut and create oversized and oval holes in the bone. These oversized and oval holes remove valuable bone that the screws require to get a good, solid purchase in the bone. These mistakes in creating good holes make it easier for the screws to toggle and become loose and even pull out. It is a common occurrence for screw to strip the holes out during insertion.

An additional feature of this invention that prevents the bit from side-cutting, is the dulling of the sharp leading edge of the flutes by means of a secondary grinding step. The initial manufacturing step of grinding the flutes into the body of the drillbit for the removal of the chips cut away in the drilling process, automatically creates sharp edges. Utilizing a following process of removing the sharp, leading edge of the flutes, the ability to side cut into the bone is removed. By making the bit end-cutting only it can automatically drill round straight and on-size holes in the bone, even regardless of slight changes in direction of the power drill not realized by the surgeon which is very common.

Unrestricted chip removal up the flutes—keeping the flutes clear—is significant to the pressure required to advance the bit through the bone with as little pressure as possible to prevent plunging out the back side of the bone. Clinical tests have proven that this additional control attributed to this new drill bit contributes greatly in preventing plunging and damaging soft tissues.

In order to help restrict bending of a drillbit during the drilling process, prior designs have relied upon tapering of the flutes from deep at the cutting end to shallow at the opposite end of the flutes. In metal, wood and other substrates commonly drilled, the chips easily move up the flutes. Living bone is usually wet from bodily fluids which allows the chips to pack and resist flowing up the flutes unlike other substrates do as mentioned. The present invention provides constant volume capacity of the chip removal flutes to allow the chips to flow unrestricted up the flutes without getting stuck and plugged up.

To overcome this common occurrence, this invention includes a new flute design that gets wider as it progresses up the shank to maintain an adequate and unrestricted space for chips to easily move upward. This prevents the chips from being compressed into a smaller opening while maintaining the tapered depth of the flutes for strength. Prior art spiral flutes utilize centrifugal force to help evacuate the chips from the flutes as the bit spins at high RPM. Wet chips respond poorly to this force and rely mostly on the constant addition of new chips being cut to force the previously cut chips to move up the flutes. These progressively wider flutes going up the shank helps prevent packing which results in less heat and cutting pressure.

The drive end of the drill bit requires a commonly used quick connector called an "AO spring loaded chuck". This connector allows the surgeon to quickly and easily connect a drillbit into a spring loaded chuck mounted to the drive end of the power drill. This novel process of starting with two different diameters of stainless steel alloys helps greatly to keep the cost down to the end user even though it has many enhanced features for this novel drill bit design. By producing these bits in two separate parts and then securing them preferably permanently together with a mechanical crimping method which forces some of the metal inside the bore of the connector to flow into a pre-formed recess near the end of the shank. This manufacturing method helps reduce the raw material cost significantly.

The overall objects of the current invention is to assure a round non-ovular, oversized hole to be drilled into living bone with less cutting pressure, easy to start in the desired location at required angles to the surface without the bit sliding to a new location.

It is an object of the present invention to provide a drillbit that produces substantially round holes in living bone.

It is an object of the present invention to form a single sharp point at the end of the bit between diametrically opposed cutting lips to provide a stable entry point for the drillbit to start cutting on various non-flat surfaces and at certain angles to the surface and to prevent the bit from walking on the surface as is common with prior art.

It is an object of the present invention to strategically form relief angles under the cutting lips to enhance the sharpness of the cutting lips. This helps provide sharper cutting edges so the drill can start cutting in the exact spot and angle required by the surgeon.

It is an object of the present invention following the start of the drilling process that the distal edges of the cutting flutes where they merge with the outside diameter of the bit, the corner of the junction be formed as a radius instead of a single point. In all prior designs, it has always been that part of the cutting edges that becomes dull first because it is this part of the cutting surfaces spinning at the highest RPM and with the greatest amount of friction as compared to the remaining, inboard cutting features which are smaller in diameter and rotate with less surface feet per minute.

It is an object of the present invention that this radius of this outside diameter of the cutting flutes is posed to create relief behind the leading edge to assure the leading edge is the highest part creating a sharp cutting edge.

It is an object of the present invention for chip removal flutes to be diametrically opposed from each other and greatest in depth starting at the cutting end and decreasing in depth for a distance towards the shank end on the drill bit.

It is an object of the present invention to also prevent the decrease in chip holding volume, the flutes also become wider as the chips flow away from the end cutting edges.

It is an object of the present invention to dull the leading edges of the chip removal flute downstream from the radius transition portion of the cutting tip to help prevent the chip removal flute portion from side cutting and oversizing the hole.

It is an object of the present invention to provide a drillbit that will cut easier and fast with less cutting pressure to help prevent plunging through the far side of the bone which causes significant damage to veins, arteries, muscles, tendons and other soft tissues or bones that may be in the path of the drill bit behind the targeted bone.

It is an object of the present invention to present a drill bit with much improved cutting ability that reduces heat common to any drilling process that can cause heat necrosis to the living bone surrounding the drilled hole. This is caused by poor cutting drillbits that can induce significant friction, resulting in dangerous high temperatures. It only requires 112° F. to kill bone. The end result can be faster and better healing of the surgical procedure.

It is an object of the present invention to increase the lifecycle of the drill bit which can reduce cost and waste by presenting better cutting edges that will stay sharp longer, while doing less damage to the surgical site.

It is an object of the present invention to present a drill bit made in two sections that are later connected by mechanical crimping of the adapter onto the drill bit shank.

It is an object of the present invention to present a means of preparing a notch in the shank of the drill bit where the metal of the adapter can flow into the notch under the load of the mechanical, compressive force of the crimping dies.

It is an object of the present invention to present a notch that will prevent rotation between the drill bit and the adapter while also prevent pullout of the drill bit from the adapter.

It is an object of the present invention to present a 2-piece orthopedic drill bit that can be produced with less waste of expensive alloys at a lower cost to the end user.

These and other features, aspects, and advantages of the present invention will become better understood with regard to the following description, appended claims, and accompanying drawings.

DETAILED DESCRIPTION OF VARIOUS EMBODIMENTS

Figure 1:
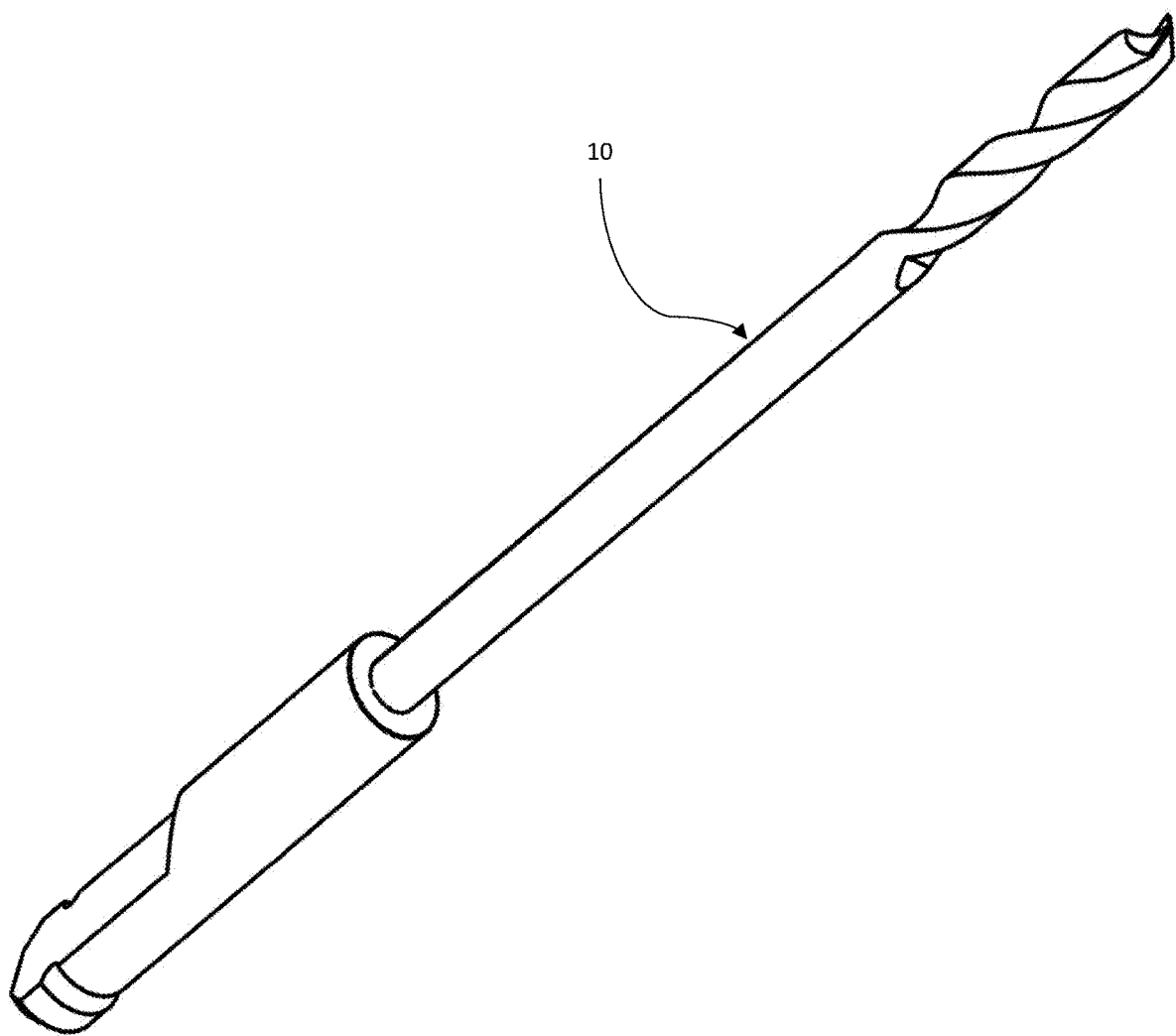
FIG. 1 is a side view of the complete drillbit including the adapter according to the present invention.

Considering the drawings, wherein like reference numerals denote like parts throughout the various drawing figures, reference numeral 10 is directed to the assembled drillbit according to the present invention.

Figure 2:
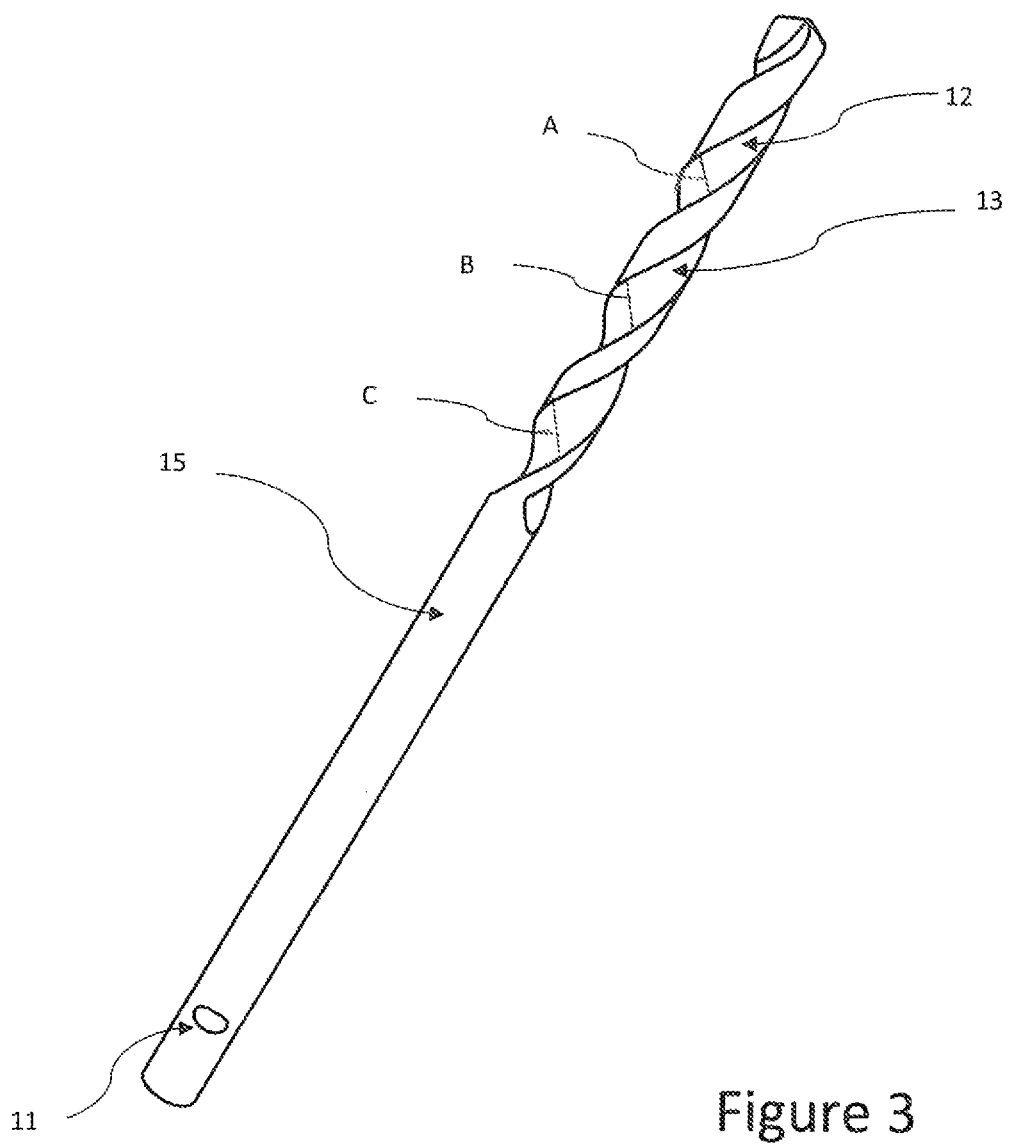
FIG. 2 is a side view of just the drillbit according to the present invention.

Referring now to FIG. 1, and FIG. 2, show a drillbit 10 having helical flutes 12 and 13 cut into shank 15. Helical flutes 12 and 13 are channels cut into the shank for removal of bone fragments created by the end cutting sharp edges created by the convergence of two formed surfaces 14 (FIG. 4) separated by sharp point 18. Therefore, when rotated against the bone the bone fragments travel up the flutes 12 and 13 allowing the forward movement of the drill bit 10 through the bone. Furthermore, the shank portion 15 follows the drill bit 10 in a straight trajectory through the bone. To prevent the leading edges 23 (FIG. 4) of flutes 12 and 13 drill bit 10 (FIG. 1) from having leading edges sharp enough to provide side cutting capability as the drill bit rotates in a clockwise direction, as standard drill bits do, these sharp edges at the transition edges of the flutes 12 and 13 with shank 15, created during the flute grinding processes, are dulled by a secondary grinding step to create dulled leading edges 25. This assures that this drill bit can only end cut, thereby avoiding all side cutting capabilities that could oversize or cause oblong or oval drilled holes.

Yet another significant feature of FIG. 2 are the increasing widths of flutes 12 and 13 as they progress away from the cutting end as referenced by alpha characters A, B and C, wherein width C is greater than width B, and width B is greater than width A. The constant widening of flutes 12 and 13 as they extend away from the cutting end, work to balance the chip removal volume capacity of flutes 12 and 13 as these flutes 12 and 13 also decrease in depth as they move away from the cutting end where they are the deepest. This novel approach to managing chip removal facilitates rapid chip removal and prevents chip packing along the length of the flutes.

Figure 3:
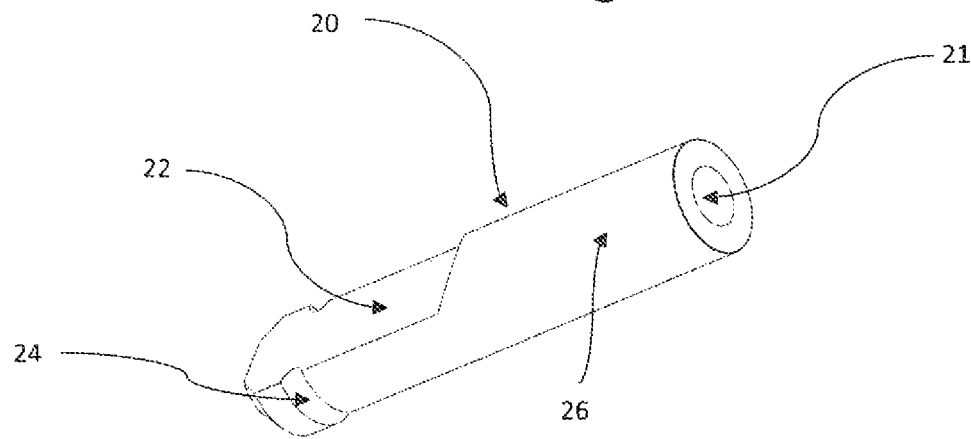
FIG. 3 is a side view of just the adapter according to the present invention.

FIG. 3 reveals an isometric view of the adapter for driving drill bit 10. Once slipped over drill bit shank 15 (FIG. 2) the assembly is placed in between a set of special crimping dies. Hydraulic pressure is applied to the crimping dies forcing them together to compress the metal onto the shank of the drillbit. Notch 11 is formed into shank 15 to allow some of the stainless steel of adapter 26 to flow into the notch 11 while under crimping pressure. An additional notch (not shown) may be provided on the shank 15 opposite the notch 11. Flat surface 22 (FIG. 3) matches a protuberance inside the industry standard, quick change AO spring loaded chuck used by most surgeons, preventing rotation of the adapter within the AO spring loaded chuck. Locking groove 24 also mates with locking lugs inside the AO spring loaded chuck to prevent the adapter from sliding out of the end of the chuck.

Figure 4:
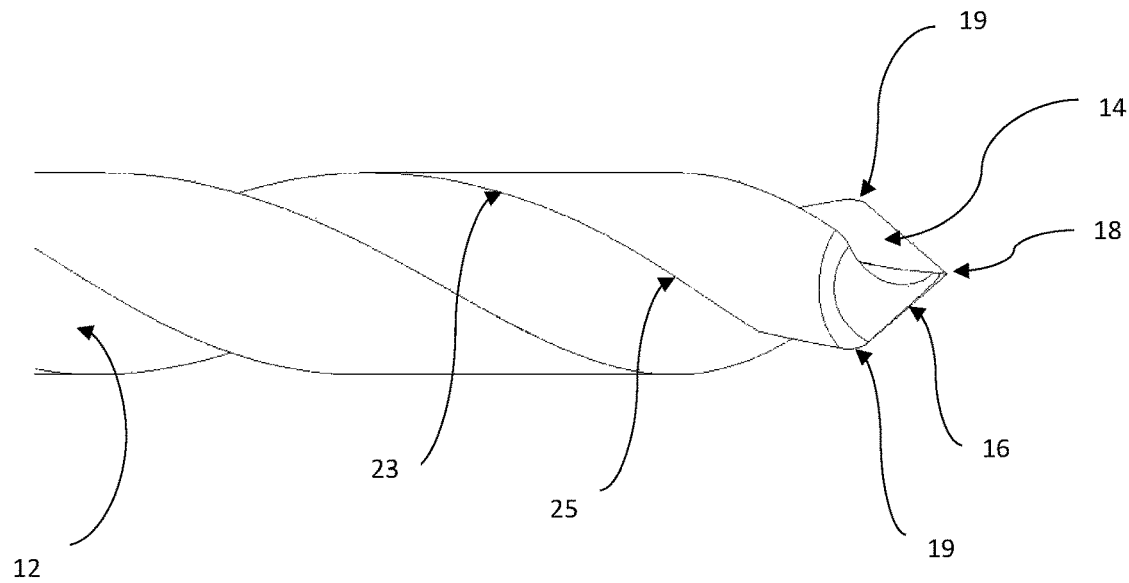
FIG. 4 is a close up side view of the features of the cutting end of the drill bit.

FIG. 4 defines a planar view of the cutting features of the drillbit and flutes. The convergence of cutting lips 16 define a sharp point 18 providing a precise starting point for the drillbit in much the same way as a center punch creates a starting point for a drill bit in metal. This prevents the drill bit from walking on the uneven surfaces of the bone at required angles to the surface that are greater or less than 90 degrees from perpendicular to the surface of the bone which occurs in most surgical operations. This remedies an age old issue known to surgeons.

Figure 5:
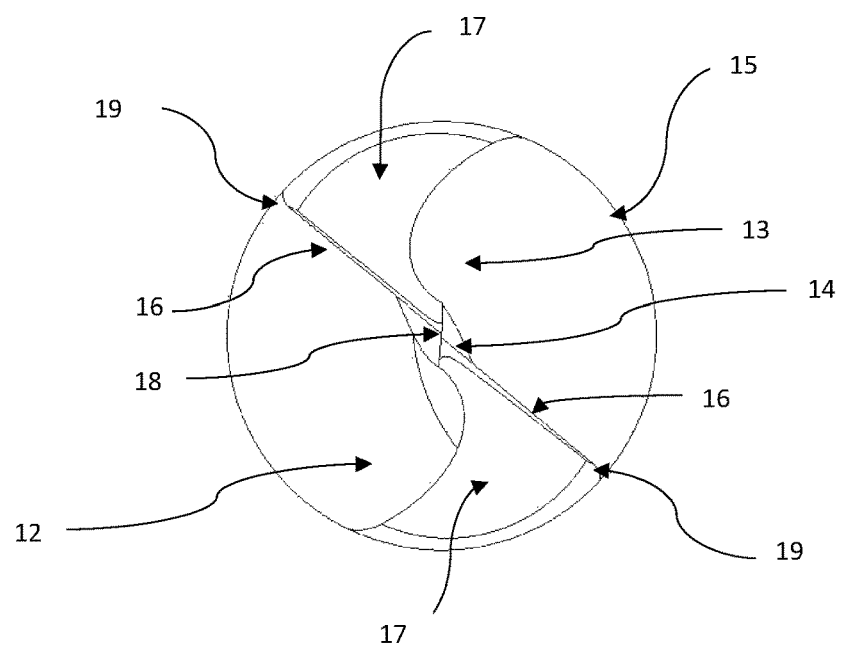
FIG. 5 is a close up, end view of the cutting end of the drill bit.

FIG. 5 shows relief surfaces 17 that provide clearance for the trailing edges behind cutting lips 16 to prevent drag and restrict cutting action of cutting lips 16. Radius transitions 19 blend cutting lips 16 and flute edges 23 as opposed to a common angled transition, this radius transition increases the useful life of the drill bit as compared to standard drill bits that transition with angles that become dull quickly. In this novel feature, the cutting friction is spread over a larger surface areas and not focused on single small points found in prior art. This increase in the useable life cycle of the drill bit and is one of the most important novelties of this invention. Drill bits that stay sharp reduce cutting pressure and help to prevent harmful plunging out the back side of the bone.

Figure 6:
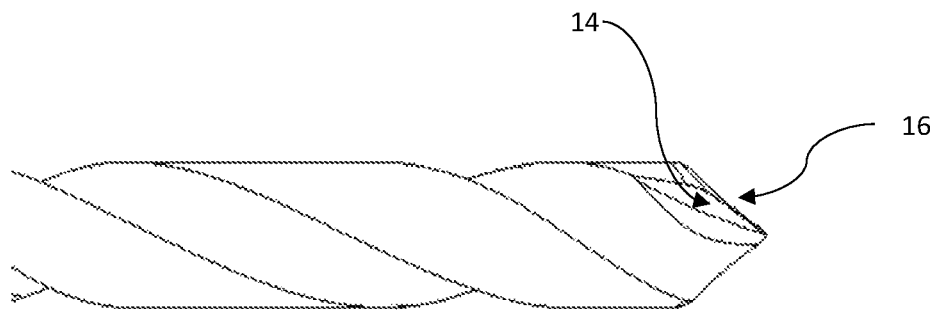
FIG. 6 is a slightly different perspective that shows a better view of two features

FIG. 6 is another view showing undercut 14 that defines a positive rake angle under cutting lips 16 for increased sharpness to increase cutting speed and reduce cutting pressure to move the bit deeper into the bone.

Figure 7:
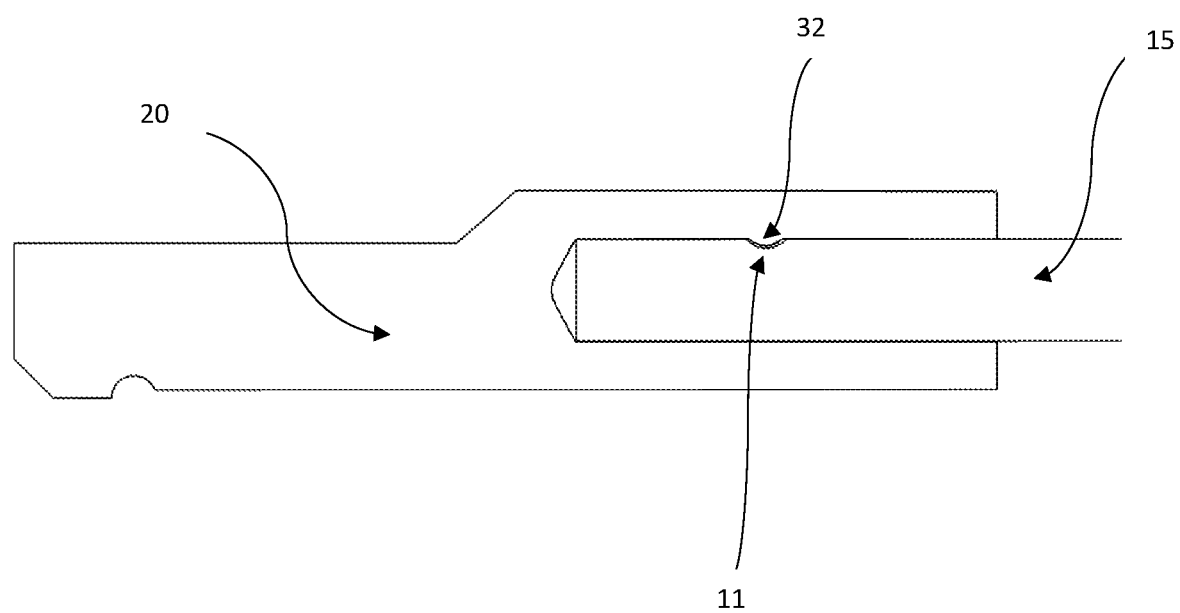
FIG. 7 is a sectional view of the connector for the AO spring loaded chuck.

FIG. 7 refers to a sectioned view of the adapter 26 with the drill bit shank 15 seated into the bore 21. The crimping action causes metal 32 to flow into notch 11 in shank 15. This prevents the adapter 26 from rotating on shank 15 and from slipping off of shank 15 during use.

It will be understood that the above-described embodiments of the invention are illustrative in nature, and that modifications thereof may occur to those skilled in the art with the benefit of the teachings of this specification, without departing from the scope and spirit of the invention as defined by the appended claims. Accordingly, this invention is not to be regarded as limited to the embodiments disclosed herein, but is to be limited only as defined in the appended claims.

I claim:

1. An orthopedic drill bit comprising:
   two flutes extending helically along a length of the orthopedic drill bit;
   two relief surfaces diametrically opposed to one another and formed directly between the two flutes, the two relief surfaces each defining a cutting lip such that the cutting lips are diametrically opposed to one another and a radiused periphery formed at a junction between distal edges of the relief surfaces and an outside diameter of the orthopedic drill bit, the radiused periphery thereby being arranged to form a blended and radiused corner between each of the cutting lips and a respective edge of the flutes; and
   a cutting head formed to include the diametrically opposed cutting lips leading to a central point arranged at a cutting end of the drill bit and away to the radiused periphery so as to center said bit.

2. The orthopedic drill bit of claim 1, wherein a width of the flutes changes downstream from the cutting end to promulgate bone shard exit.

3. The orthopedic drill bit of claim 1, wherein a width of the flutes increases downstream from the cutting end to promulgate bone shard exit.

4. The orthopedic drill bit of claim 1, wherein a drive end of the drill bit opposing the cutting end comprises an AO quick connect coupler fixedly attached thereto.

* * * * *